United States Patent
Brumer et al.

(10) Patent No.: US 6,402,898 B1
(45) Date of Patent: Jun. 11, 2002

(54) COHERENTLY CONTROLLED LASER DISTILLATION OF CHIRAL ENANTIOMERS

(75) Inventors: Paul Brumer, Toronto (CA); Moshe Shapiro; Einat Frishman, both of Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/628,681

(22) Filed: Jul. 28, 2000

Related U.S. Application Data

(60) Provisional application No. 60/145,938, filed on Jul. 28, 1999.

(51) Int. Cl.[7] .................................................. C07C 7/00
(52) U.S. Cl. .............................. 204/157.61; 204/157.15
(58) Field of Search ........................ 204/157.15, 157.61

(56) References Cited

PUBLICATIONS

Salam et al., "On the Relative Populations of Excited State Enantiomers, for Randomly Oriented Molecules, Obtained Through the Use of Circularly Polarized Pulsed Lasers", Chem. Phy. Let., vol. 277, pp. 199–207. (no month available) 1997.*

Shapiro et al. "Controlled photon induced symmetry breaking: Chiral molecular products from achiral precursors", $J,$. Chem. Phys., vol. 95, No. 11, pp. 8658–8661, (1991) * no month available.

Oreg et al., "Adiabatic following in multilevel systems", Physical Review A, vol. 29, No. 2, pp. 690–697, (1984) * no month available.

Kuklinsi et al., "Adiabatic population transfer in a three–level system driven by delayed laser pulse", Physical Review, vol. 40, No. 1, pp. 6741–6744, (1989) * no month available.

Gaubatz et al., "Population transfer between molecular vibrational levels by stimulated Raman scattering with partially overlapping laserfields. A new concept and experimental results", J. Chem. Phys., vol. 92, No. 9, pp. 5363–5376, (1990) * no month available.

* cited by examiner

Primary Examiner—Edna Wong
(74) Attorney, Agent, or Firm—Browdy and Neimark

(57) ABSTRACT

A laser-based method of enhancing the enantiomeric excess of one chiral enantiomer in a mixture of chiral enantiomers, denoted L and D (and related to one another by the inversion operation I), is described. The molecule L and D is chosen so that electronic excitation is to an electronically excited species with stationary ro-vibrational states which are individually either symmetric or anit-symmetric with respect to I. The mixture is irradiated with a series of achiral pulses of coherent laser light. By varying the frequencies, timing, and durations of these pulses one can selectively increase the enantiomeric excess of either L or D in the ground electronic state.

10 Claims, 7 Drawing Sheets

COHERENTLY CONTROLLED LASER DISTILLATION OF CHIRAL ENANTIOMERS

Figure 1:
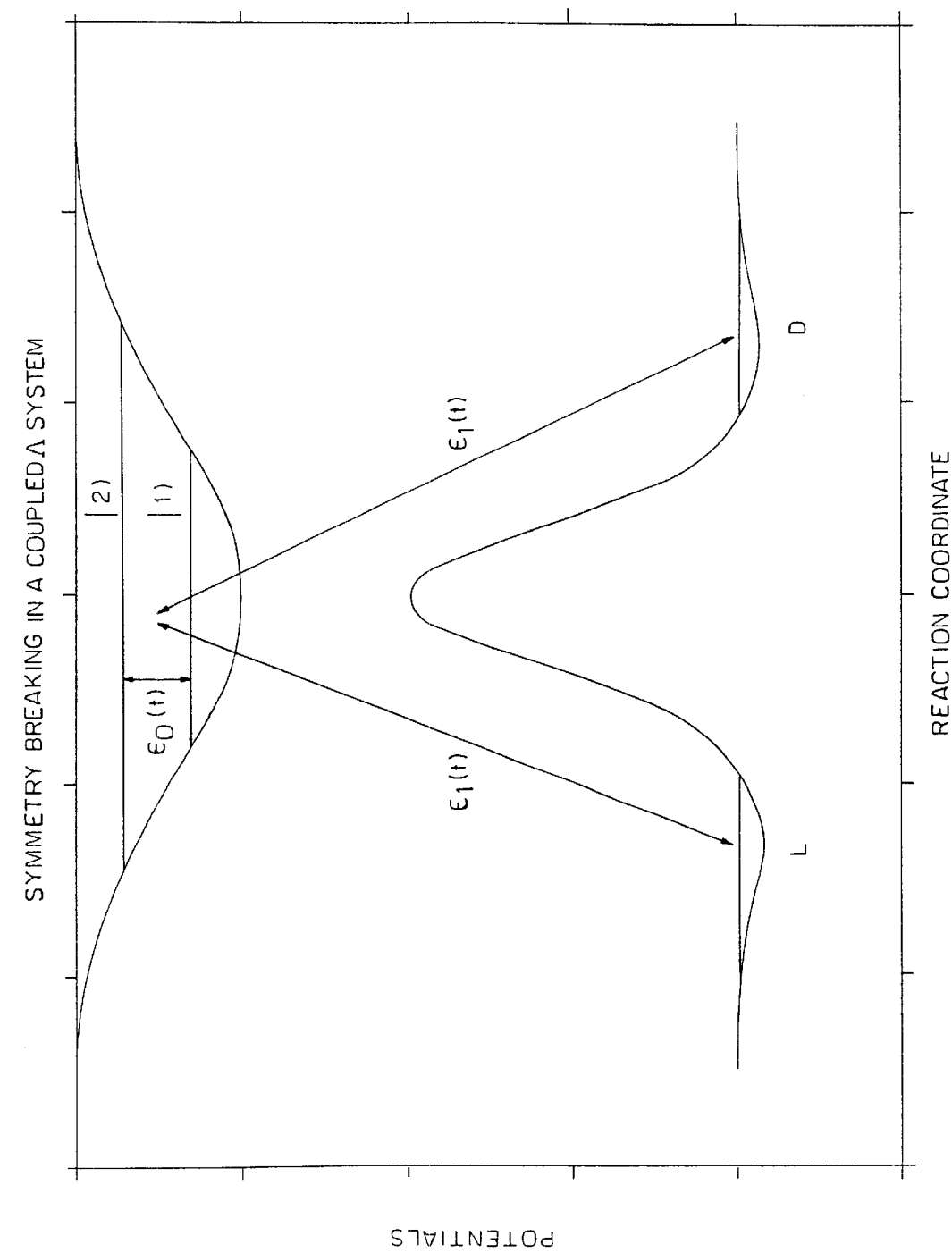

This application claims the benefit of Provisional Application Ser. No. 60/145,938, filed Jul. 28, 1999.

FIELD OF THE INVENTION

This invention relates to a method of using achiral pulsed laser irradiation to enhance the amount of a particular chiral enantiomer in an enantiomeric mixture. More particularly, the invention relies upon controllable quantum interference effects generated in the system by multi-photon processes to alter the ratio of chiral enantiomers.

BACKGROUND AND SUMMARY OF THE INVENTION

Chemical reactions which begin with achiral molecules in an achiral environment are incapable of producing reaction products which favor production of one enantiomeric product, e.g. L, over its mirror image D. In addition, the physical and chemical properties of two chiral enantiomers are similar, preventing the enhanced production of L over D by any direct chemical or physical method which relies upon achiral ingredients. However, the desire to produce a specific chiral enantiomer in preference to its mirror image, called asymmetric synthesis, is a longstanding challenge in synthetic chemistry. In particular, there is a great deal of interest in doing so for the production of stereospecific pharmaceuticals.

A number of methods are available to perform asymmetric synthesis. However, all rely upon the introduction, in the chemical reaction, of some chiral component (e.g. a chiral reagent, chiral enzyme or chiral template). By sharp contrast, the method proposed here requires neither an overall chiral initial molecular system nor chiral laser excitation. Rather, it relies upon the fact that the pulsed laser excitation of the D and L systems to the species in the excited electronic state can prepare a superposition of vibrational-rotational states which no longer possess the reflection symmetry of the excited molecular species. This superposition state differs if it is prepared from D or from L, allowing a laser-based method of differentiating between L and D and of enhancing the concentration of one enantiomer over another.

We note that alternative ideas, based on laser excitation, have been advanced. These methods all rely upon using chiral light (e.g. circularly polarized light) where the effects rely on high order perturbation theory, tend to be weak and hence without practical utility. We further note that our approach are peripherally related to established optical pumping scenarios studied in Quantum Optics. However, none of the Quantum Optics work focuses on the issue of enhancing the enantiomeric ratio nor does it provide a method for altering enantiomeric ratios.

Finally, note that is past work we considered the photodissociation of a molecule LAD, where A is an atom or molecule, to produce a controlled ratio of LA+D vs L+AD. In that case the excitation was to a set of continuum energy levels from a bound achiral molecule LAD, quite different from the bound-bound (from the bound chiral enantiomers L and D to a bound excited species) transitions invoked here. Further, out past work relied upon small non-Franck-Condon components of the dipole operator, required a means (e.g. external magnetic fields) of separating out product states with well defined projections of the total angular momentum along a space fixed axis, required an initial step to synthesize the particular molecule LAD and L an D. Hence, our past work is totally different in both concept and execution from the present invention described herein.

It is the object of this invention to provide a novel process for enhancing the enantiomeric excess of one chiral enantiomer over another in a mixture of chiral enantiomers.

The present invention is a laser-based method of enhancing the enantiomeric excess of one chiral enantiomer in a mixture of chiral enantiomers, denoted L and D (and related to one another by the inversion operation I). The molecule L and D is chosen so that electronic excitation is to an electronically excited species with stationary rotational-vibrational states which are individually either symmetric or anti-symmetric with respect to I. The mixture is irradiated with a series of achiral pulses of coherent laser light. By varying the frequencies, timing, and durations of these pulses one can selectively increase the enantiomeric excess of either L or D in the ground electronic state. In an alternate application, a molecule B is added to a mixture of L and D where B is chosen so that (a) L–B and B–D are stable geometrically distinct species on the ground electronic potential energy surface which are related to one another by inversion, and (b) LB and DB molecules are stable, achiral molecules in an excited electronic state such that LB and BD are either identical or interchange rapidly with one another. The mixture is irradiated with a series of achiral pulses of coherent laser light. By varying the frequencies, timing, and durations of these pulses one can selectively increase the enantiomeric excess of either LB of BD in the ground electronic state. Subsequent traditional chemistry strips the B to yield an excess of either L or D.

The advantages of this invention over previous approaches is considerable. First, only a minimal amount of chemistry is required to enhance the desired enantiomer whereas other asymmetric synthesis schemes require large numbers of complex chemical steps. Second, this process can serve as the final step in the chemical synthesis of a wide variety of molecules. That is, having synthesized a mixture of D and L compounds in traditional synthetic schemes, one can, assuming property molecular characteristics, add this process as an additional step to enhance the enantiomeric excess of the product. Hence this approach is applicable to the production of chiral enantiomers of a wide variety of molecules.

A BRIEF DESCRIPTIONS OF THE DRAWINGS

FIG. 1: Illustrates a sample Laser Distillation Scenario, here termed the "Coupled Double Lambda System". A laser, with frequency $\omega_1$ and pulse envelope $\epsilon_1(t)$ couples, by virtue of the dipole operator, the states of the D and L enantiomers to two vibrotational states $|1\rangle$ and $|2\rangle$ in the excited electronic manifold. A second laser pulse with envelope $\epsilon_0(t)$ couples excited levels $|1\rangle$ and $|2\rangle$.

Figure 2:
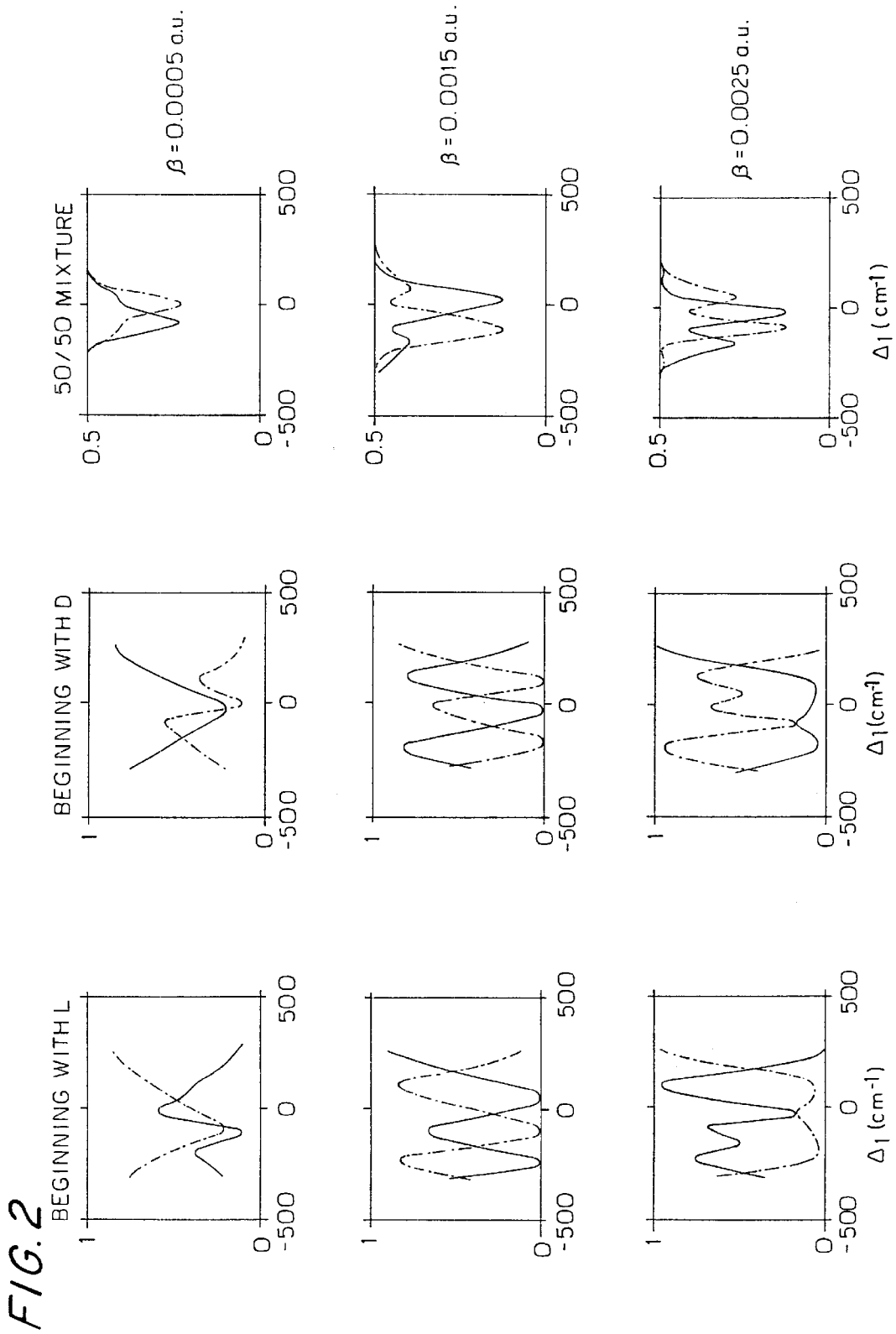

FIG. 2: Illustration of the probabilities of populating the $|D\rangle$ (solid lines) and $|L\rangle$ (dot-dash lines) states in the Coupled Double Lambda system after laser excitation, but prior to radiative emission. Computations here show three different cases, corresponding to three different initial conditions: (1) only state $|D\rangle$ occupied; (2) only state $|L\rangle$ occupied, and (3) both $|D\rangle$ and $|L\rangle$ equally occupied. In addition, results are shown for three different laser powers (both pulses are taken to be of the same intensity), $\beta \equiv \beta_0 = \beta_1 = 5 \times 10^{-4}$, $1.5 \times 10^{-3}$ and $\beta = 2.5 \times 10^{-3}$ where Gaussian pulses are assumed with $\alpha_1 = \alpha_0 = 0.15$ psec, with $t_0 = t_1$. The remaining system parameters are taken, in this model system, as: $<1|\mu^{(1)}|D>=<1|\mu^{(1)}|L>=1$ a.u., $<2|\mu^{(1)}|L>=-<2|\mu^{(1)}|D>=1$ a.u., $<1|\mu^{(0)}|2>=1$ a.u., $\omega_{2,1}=100$ cm$^{-1}$. Results are shown as a function of the detuning, $\Delta_1$ of the first pulse with respect to level 1. The second pulse is taken to be exactly tuned to the transition between levels 1 and 2.

Figure 3:
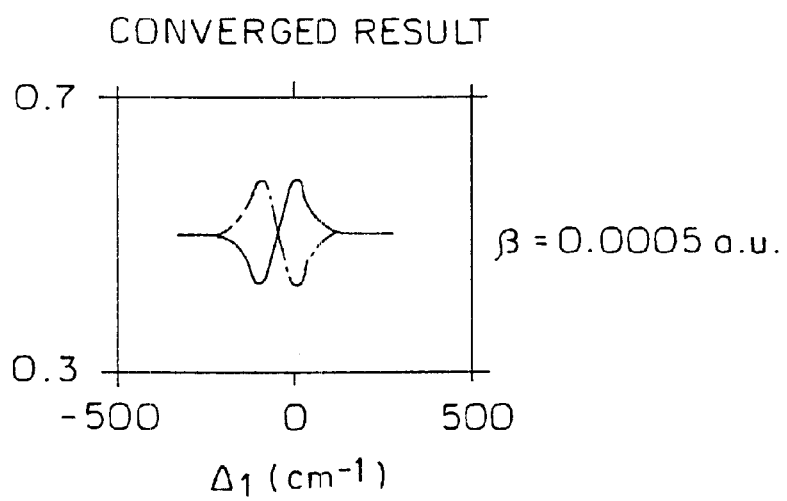
Figure 3:
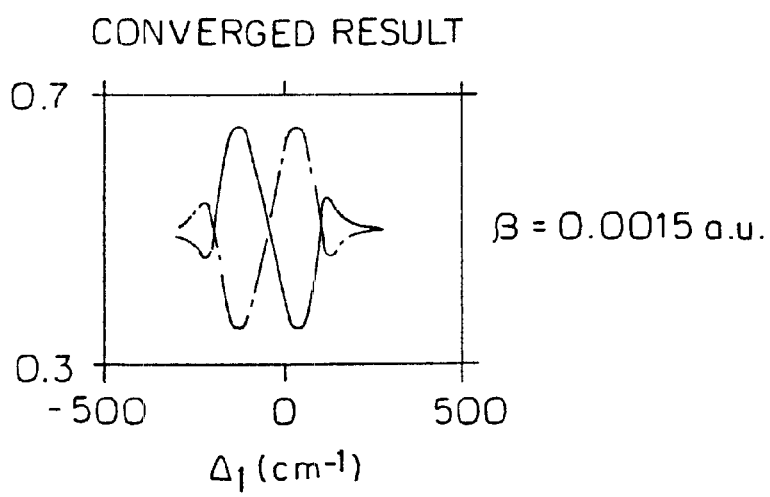
Figure 3:
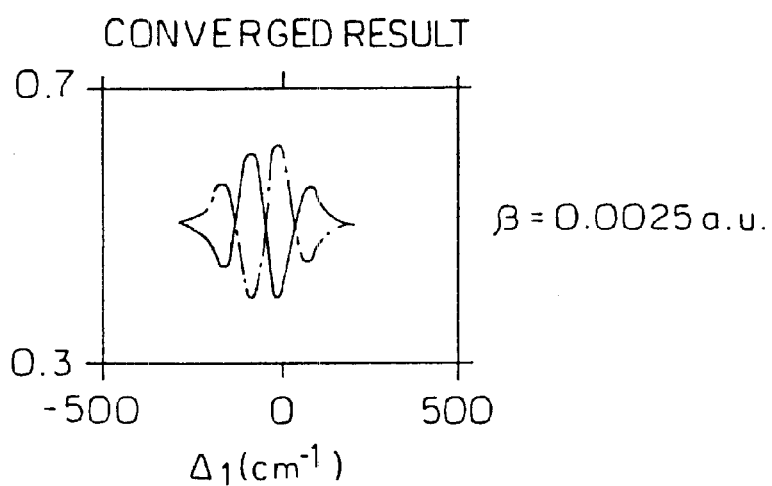

FIG. 3: Results for the cases described in FIG. 2 but where the system has gone through a convergent series of steps comprised of radiative excitation, followed by collisional and radiative relaxation.

Figure 4:
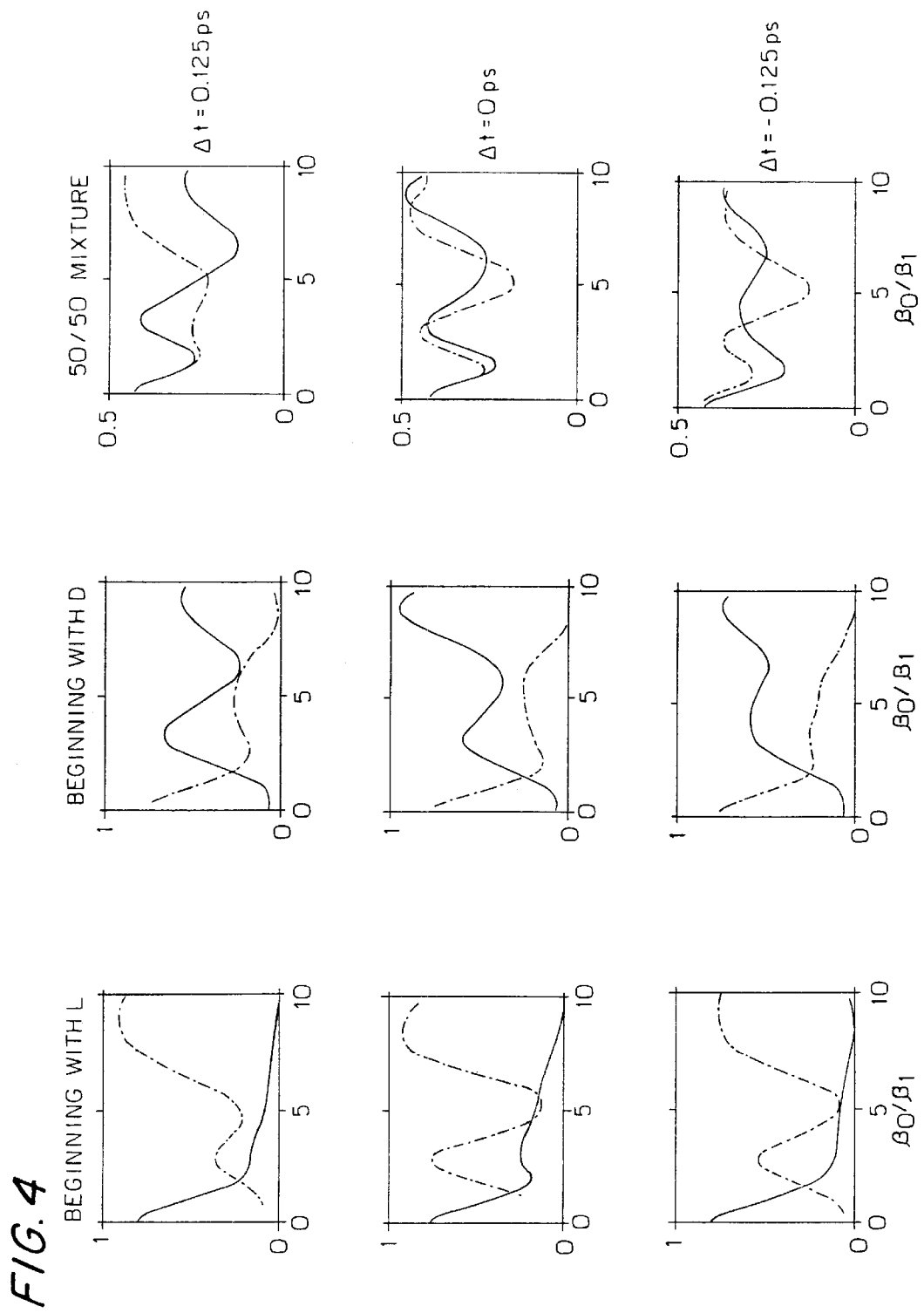

FIG. 4. Illustration of the probabilities of populating the |D> (solid lines) and |L> (dot-dash lines) states in the coupled Double Lambda system after laser excitation, but prior to radiative emission, as a function of $\beta_0/\beta_1$, with $\beta_1=1\times10^{-4}$ a.u. Computations here show three different cases, corresponding to three different initial conditions: (1) only state |D> occupied; (2) only state |L> occupied, and (3) |D> and |L> equally occupied. In addition, results are shown for three different values of $\Delta t$. System parameters are as in FIG. 1 with $\alpha_1=\alpha_0=0.25$ psec, $\Delta_1=0$ cm$^{-1}$ and $\Delta^{(2)}=0$.

Figure 5:
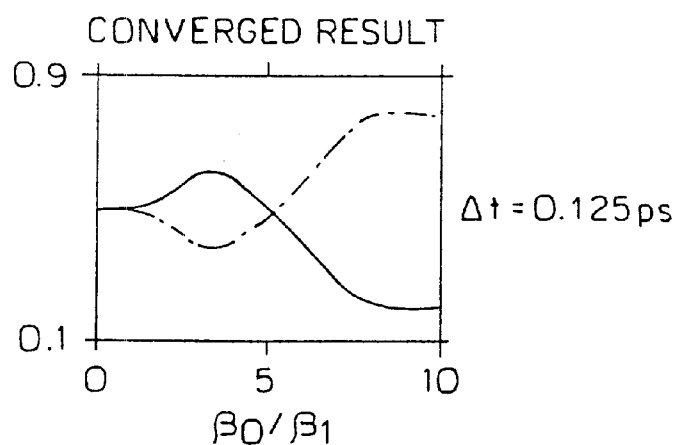
Figure 5:
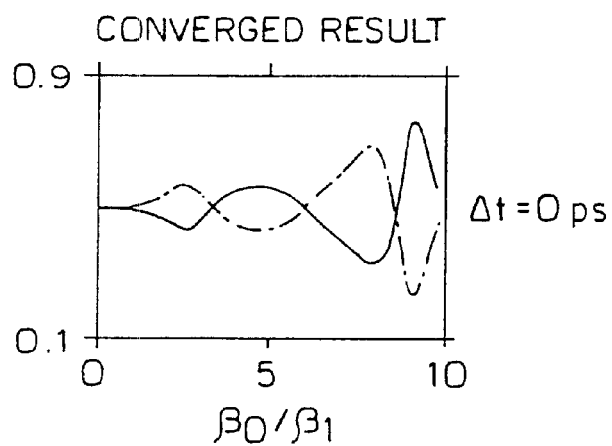
Figure 5:
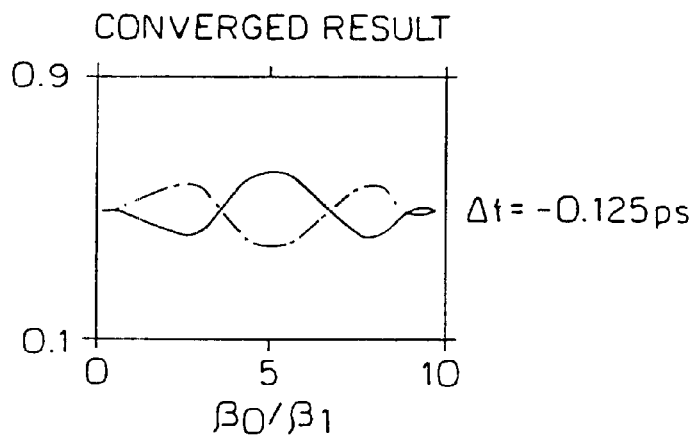

FIG. 5: Results for the cases described in FIG. 4 but where the system has gone through a convergent series of steps comprised of radiative excitation, followed by collisional and radiative relaxation.

Figure 6:
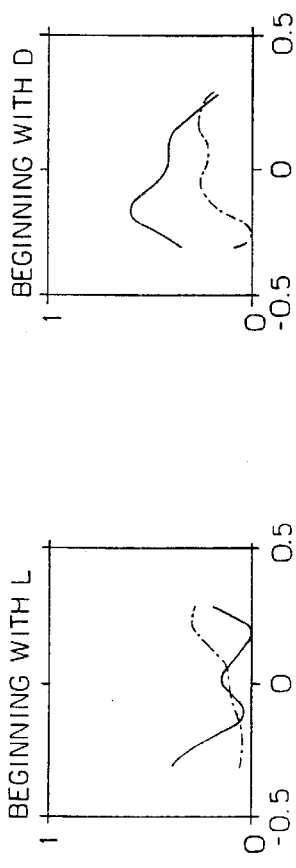
Figure 6:
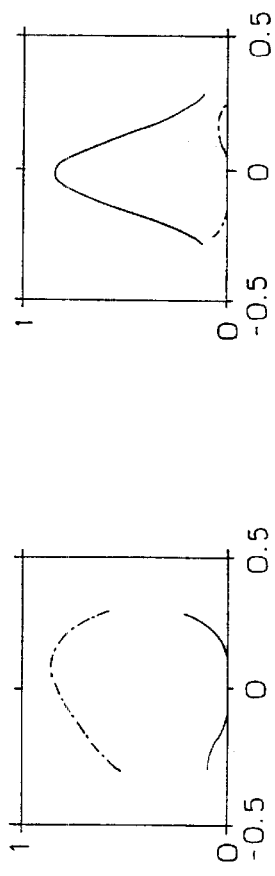
Figure 6:
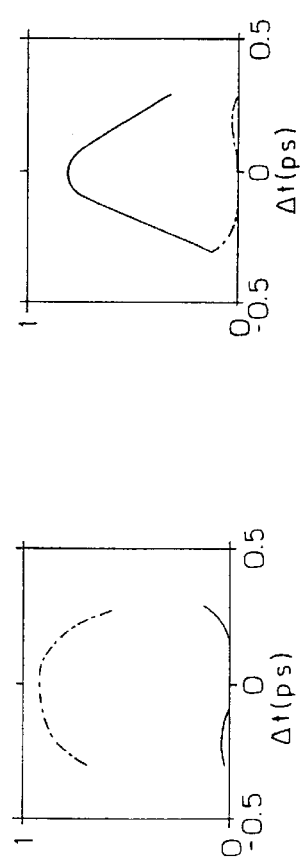
Figure 6:
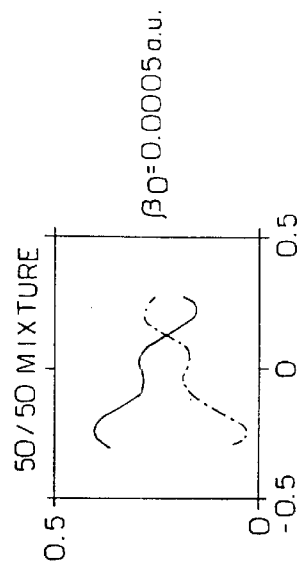
Figure 6:
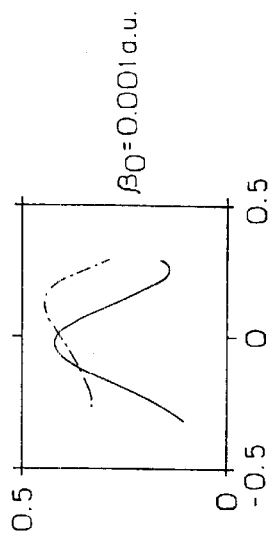
Figure 6:
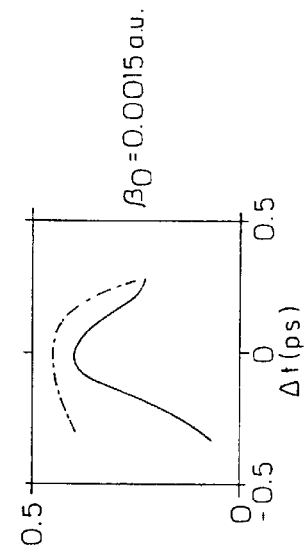

FIG. 6: Illustration of the probabilities of populating the |D> (solid lines) and |L> (dot-dash lines) states in the Coupled Double Lambda system after laser excitation, but prior to radiative emission, as a function of $\Delta t$. Computations here show three different cases, corresponding to three different initial conditions: (1) only state |D> occupied; (2) only state |L> occupied, and (3) both |D> and |L> equally occupied. In addition, results are shown for three different values of $\beta_0$ with system parameters as in FIG. 1 and with $\alpha_1=\alpha_0=0.25$ psec, $\beta_1=1\times10^{-4}$ a.u., $\Delta_1=0$ cm$^{-1}$, and $\Delta^{(2)}=0$.

Figure 7:
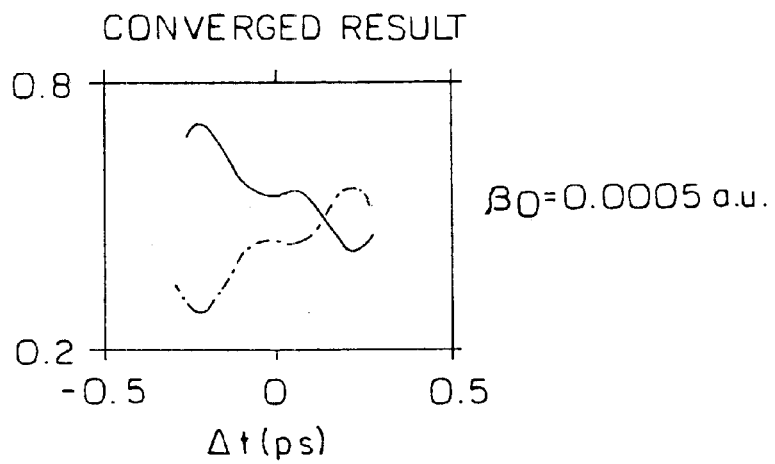
Figure 7:
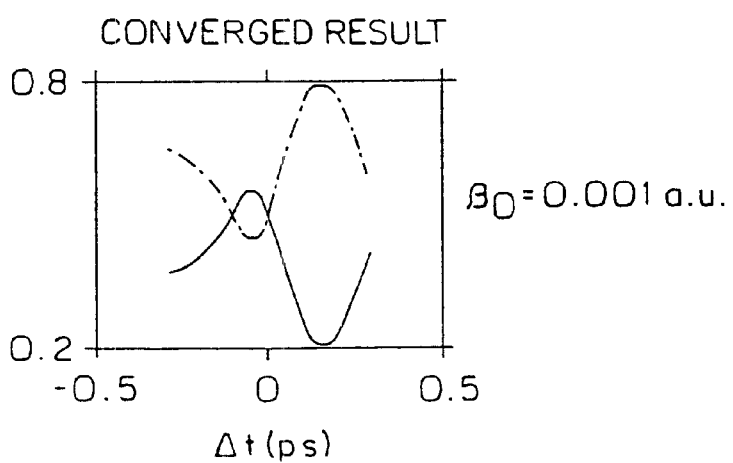
Figure 7:
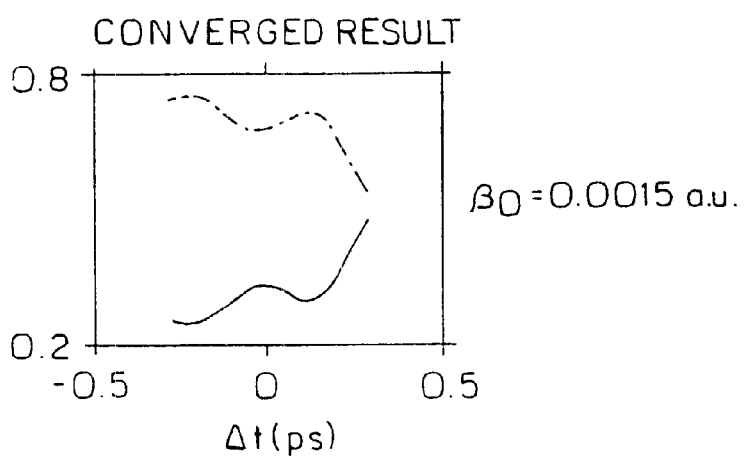

FIG. 7: Results for the cases described in FIG. 6 but where the system has gone through a convergent series of steps comprised of radiative excitation, followed by collisional and radiative relaxation.

characteristics of the laser pulses (coherence, pulse timing, frequencies, pulse frequencies, frequency widths, etc.). In addition, the thermodynamic characteristics of the L, D mixture (e.g. temperature, concentrations, pressure, volume) will also affect the final enantiomeric ratio. We term this overall method "Laser Distillation of Chiral Enantiomers".

In cases where the molecules L and D are not themselves suitable to this procedure we can, as a general example, proceed in the following way. We add a molecule B to the L, D mixture to form weakly bound species L–B and B–D, which are also right and left handed enantiomeric pairs (i.e. L–D and B–D now serve as the molecules L and D of the general scenario). The reagent B is chosen so that electronic excitation of B–D and L–B forms an excited species G which has stationary ro-vibrational states which are either symmetric or antisymmetric with respect to inversion through I. The mixture of L–B and B–D is then irradiated with a well defined sequence of laster pulses to form a superposition of ro-vibrational states of the electronically excited G species. This excited system then radiates energy to return to the ground electronic state of L–B and B–D. By successively irradiating the system and the allowing radiative emission and collisional relaxation one can enhance the concentration of either enantiomer L–B or B–D by varying the characteristics of the laser pulses (coherence, pulse timing, frequencies, pulse frequencies, frequency widths, etc.). In addition, the thermodynamic characteristics of the L, B, D mixture (e.g. temperature, concentrations, pressure, volume) will also affect the final enantiomeric ratio. Subsequent traditional chemistry is used to remove the B from the system, leaving enantiomerically enriched L or D. Note that the B molecule is completely recovered and can be reused to enrich other mixtures of L and D.

As a particular example of the latter approach, L and D might be the left and right handed enantiomers of a chiral alcohol, and B is the ketone derived from this alcohol. Then the kinetics on the ground electronic state is then

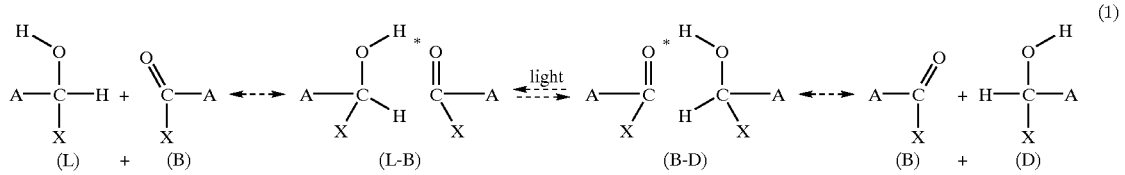

(1)

DESCRIPTION OF PREFERRED EMBODIMENTS

Consider the case where we have a mixture of molecules L and D and where we denote the common species resulting from electronic excitation of either L or D as G. Note that there exists a plane of symmetry, denoted I, such that inversion of L through the plane produces D. The stationary vibrotational states of L and D are neither symmetric nor antisymmetric with respect to I but the system is chosen such that G possesses stable states that are symmetric or asymmetric with respect to inversion through I. The mixture of L and D is then irradiated with a well defined sequence of achiral laser pulses, to form a superposition state of ro-vibrational states of G. This excited system then radiates energy to return to the ground electronic state of L and D. By successively irradiating the system, and then allowing radiative emission and collisional relaxation, one can enhance the concentration of either enantiomer L or D by varying the where A and X are distinct organic groups and * denotes a Hydrogen Bond. Here the alcohol and ketone exchange two hydrogen atoms so as to produce the ketone, but with an alcohol of reverse handedness. In this instance the electronically excited species G, which is formed upon excitation with light, is given by

(G)

Note that the top-most and bottom-most Hydrogens are attached to the Oxygens and Carbons, respectively, by "half-bonds".

The invention relies upon the interaction between the L and D molecules with two or more electromagnetic fields to produce a different excited vibrational superposition state of the excited electronic species G, depending on whether excitation was from L or D. The theoretical underpinnings for this approach, developed for a number of different scenarios, are described below.

Consider the time dependent Schrödinger Equation describing the dynamics of a molecule, with Hamiltonian $H_M$ in the presence of a series of laser pulses. In general we may deal with lasers which are not fully coherent but for simplicity we focus here on transform limited pulses. The electric field associated with a transform limited laser source is given by:

$$E(t) = \sum_k E_k(t), \qquad (3)$$

where $$E_k(t) \equiv 2\hat{\epsilon}_k R_e \epsilon_k(t) \exp(i w_k t), \qquad (4)$$

where $\epsilon_k(t)$ being the time dependent laser pulse envelope, $w_k$ is the central laser frequency and $\hat{\epsilon}_k$ is the polarization direction. The time dependent Schrödinger Equation is given by:

$$\hbar \partial |\Psi\rangle / \partial t = H_{total}(t) |\Psi\rangle \qquad (5)$$

where, $$H_{total}(t) = H_M - \sum_k \vec{\mu}_k \cdot E_k(t) \qquad (6)$$

where $\vec{\mu}_k$ is the transition-dipole moment for the electronic transition induced by $E_k(t)$. To solve Eq. (5) we expand $|\Psi\rangle$ to eigenstates $|j\rangle$ of the molecular Hamiltonian [i.e. $H_M|j\rangle = E_j|j\rangle$]:

$$|\Psi\rangle = \sum_j b_j \exp(-iE_j t/\hbar)|j\rangle. \qquad (7)$$

Substituting Eq. (7) into Eq. (5), multiplying by $\langle i|$ to integrate over molecular coordinates given the standard set of coupled equations:

$$\dot{b}_i = \frac{i}{\hbar} \sum_{jk} b_j \exp(-i\omega_{ji} t) \langle i | \vec{\mu}_k \cdot E_k(t) | j \rangle \qquad (8)$$

where $w_{ji}=(E_j-E_i)/\hbar$. All control scenarios follow from specific choices of the states $|j\rangle$ in Eq. (7) and functional forms for the laser fields in Eq. (3).

Coupled Double Lambda System: As an example of a laser distillation scenario consider the molecules D and L in their ground electronic states and in vibrational-rotational eigenstates $|D\rangle$ and $|L\rangle$, of energy $E_D=E_L$. We choose E(t) so as to excite the system to two eigenstates $|1\rangle$ and $|2\rangle$, of energy $E_1$ and $E_2$ of the electronically excited G. The states $|1\rangle$ and $|2\rangle$ are coupled by an additional laser field (see FIG. 1). Specifically, we choose E(t) to be composed of two pulses, $$E(t) = \sum_{k=0,1} [\varepsilon_k(t)\exp(i\omega_k t) + \varepsilon_k^*(t)\exp(-i\omega_k t)]\hat{e}_k \qquad (9)$$

where the central frequency $w_0$ is in near resonance with $w_{21} \equiv (E_2-E_1)/\hbar$,[i.e. $w_0 \approx w_{21}$] and the central frequency $w_1$ is chosen to lie between $w_{1D} \equiv (E_1-E_D)/\hbar$, and $w_{2D} \equiv (E_2-E_D)/\hbar$ (see FIG. 1). In this case, only four states are relevant and Eq. (7) becomes, $$|\Psi\rangle > b_D(t)\exp(-iE_D t/\hbar)|D\rangle + b_L(t)\exp(-iE_L t/\hbar)|L\rangle + b_1(t)\exp(-iE_1 t/\hbar)|1\rangle + b_2(t)\exp(-iE_2 t/\hbar)|2\rangle. \qquad (10)$$

Equation (8), in the rotating wave approximation, becomes $$\dot{b}_1 = i\exp(i\Delta_1 t)[\Omega_{D,1}^* b_D + \Omega_{L,1}^* b_L] + i\exp(i\Delta^{(2)}t)\Omega_0^* b_2 \qquad (11)$$

$$\dot{b}_2 = i\exp(i\Delta_2 t)[\Omega_{D,2}^* b_D + \Omega_{L,2}^* b_L] + i\exp(-i\Delta^{(2)}t)\Omega_0 b_1$$

$$\dot{b}_D = i\exp(-i\Delta_1 t)\Omega_{D,1} b_1 + i\exp(-i\Delta_2 t)\Omega_{D,2} b_2$$

$$\dot{b}_L = i\exp(-i\Delta_1 t)\Omega_{L,1} b_1 + i\exp(-i\Delta_2 t)\Omega_{L,2} b_2$$

where $$\Omega_{ij}(t) \equiv \mu_{ij}^{(1)} \varepsilon_1(t)/\hbar \qquad (12)$$

$$\Delta_j \equiv \omega_{jD} - \omega_1$$

$$\Omega_0 \equiv \mu_{21}^{(0)} \varepsilon_2(t)/\hbar$$

$$\Delta^{(2)} \equiv \omega_{21} - \omega_0$$

where $\mu_{ij}^{(k)} \equiv \langle i| \vec{\mu}_k \cdot \hat{\epsilon}_k |j\rangle$, with i=D,L and j=1,2.

The heart of the laser distillation process lies is in choosing the laser of central frequency $w_1$ so that it excites a state $|1\rangle$ which is symmetric with respect to the inversion operation I, and a state $|2\rangle$ which is anti-symmetric with respect to the same operation. To do so we can choose $\epsilon_1(t)$ to be unimodal if $|1\rangle$ and $|2\rangle$ are adjacent levels, or biomodal of the pulse needs to be shaped to predominantly excite states of the desired symmetries. Hence we have state such that $$I|1\rangle = |1\rangle, I|2\rangle = -|2\rangle. \qquad (13)$$

In addition, the structure of D and L is such that $$I|D\rangle = |L\rangle; \text{ and } I|L\rangle = |D\rangle \qquad (14)$$

Consider now the nature of the dipole transition matrix elements between $|D\rangle$ and $|L\rangle$ and $|1\rangle$ and $|2\rangle$. To do so we rewrite $|D\rangle$ and $|L\rangle$ in terms of symmetric and antisymmetric states $|S\rangle$ and $|A\rangle$. That is, $$|D\rangle = |A\rangle + |S\rangle$$

$$|L\rangle = |A\rangle - |S\rangle \qquad (15)$$

The relevant matrix elements are then of the form:

$$\langle 1|\mu^{(1)}|D\rangle = \langle 1|\mu^{(1)}|A+S\rangle = \langle 1|\mu^{(1)}|A\rangle \qquad (16)$$

$$\langle 1|\mu^{(1)}|L\rangle = \langle 1|\mu^{(1)}|A-S\rangle = \langle 1|\mu^{(1)}|A\rangle$$

$$\langle 2|\mu^{(1)}|D\rangle = \langle 2|\mu^{(1)}|A+S\rangle = \langle 2|\mu^{(1)}|S\rangle$$

$$\langle 2|\mu^{(1)}|L\rangle = \langle 2|\mu^{(1)}|A-S\rangle = -\langle 2|\mu^{(1)}|S\rangle$$

That is, $$\Omega_{D,1}=\Omega_{L,1}, \Omega_{D,2}=-\Omega_{L,2}, \quad (17)$$

Given Eq. (17), Eq. (11) becomes $$\dot{b}_1 = i\exp(i\Delta_1 t)\Omega_{D,1}^*[b_D + b_L] + i\exp(i\Delta^{(2)} t)\Omega_0^* b_2$$

$$\dot{b}_2 = i\exp(i\Delta_2 t)\Omega_{D,2}^*[b_D - b_L] + i\exp(-i\Delta^{(2)} t)\Omega_0 b_1$$

$$\dot{b}_D = i\exp(-i\Delta_1 t)\Omega_{D,1} b_1 + i\exp(-i\Delta_2 t)\Omega_{D,2} b_2$$

$$\dot{b}_L = i\exp(-i\Delta_1 t)\Omega_{D,1} b_1 - i\exp(-i\Delta_2 t)\Omega_{D,2} b_2 \quad (18)$$

The essence of the laser distillation method lies in Eq. (17) and the effect of these relationships on the dynamical equations for the level populations [i.e., in this case, Eq. (18)]. Specifically, the equation for the time evolution of $b_D(t)$ is different from the equation for the time evolution of $b_L(t)$, due to the sign difference in the last term in Eq. (18). As a result, the populations of $|D\rangle$ and $|L\rangle$, after laser excitation, are different.

Consider, for example, numerically solving Eq. (11) assuming Gaussian pulses:

$$\epsilon_l(t)=\beta_l \exp[-((t-t_l)/\alpha_l)^2] \ (l=0,1) \quad (19)$$

FIG. 2 displays the final probabilities $P_D=|b_D(\infty)|^2$, $P_L=|b_L(\infty)|^2$ in these levels, after a single pulse sequence, for a variety of pulse parameters. In particular, results are shown for various values of $\Delta_1$ at various different pulse powers assuming that one starts solely with D, solely with L, or with a racemic mixture of both enantiomers. Most relevant is that for particular parameters one can significantly enhance the population of one chiral enantiomer over the other. For example, for $\Delta_1=-125$ cm$^{-1}$, $\beta\equiv\beta_0=\beta_1=1.5\times10^{-3}$, a racemic mixture of D and L can be converted, after a single pulse, to an enantiomerically enriched mixture with predominantly D. Tuning to $\Delta_1=25$ cm$^{-1}$ at the same power results in a significant enhancement of L.

FIG. 2, however, only provides input into an overall computation of the results of the laser distillation process. In the total laser distillation process we assume that we begin with an incoherent mixture of $N_D$ molecules of type D and $N_L$ molecules of type L. In the first step the system is excited, as above, with a laser pulse sequence. In the second step, the system collisionally and radiatively relaxes so that all the population is in $|L\rangle$ and $|D\rangle$. This pair of steps is then repeated until the populations of $|L\rangle$ and $|D\rangle$ converge. To obtain the result computationally we note that the population after laser excitation, but before radiative relaxation, consists of the weighted sum of the results of two computations: $N_D$ times the results of laser excitation starting solely with molecules in $|D\rangle$, plus $N_L$ times the results of laser excitation starting solely with molecules in $|L\rangle$. If we use the notation $P_D$ and $P_L$ for the probabilities of $|D\rangle$ and $|L\rangle$ resulting from laser excitation assuming the first of these initial conditions, and $P'_D$ and $P'_L$ for the results of excitation following from the second of these initial conditions, then the populations of $|D\rangle$ and $|L\rangle$ after laser excitation of the mixture is $N_D=N_D P_D + N_L P'_D$ and $N_L=N_D P_L + N_L P'_L$. The remainder of the population $N_D[1-P_D-P_L]+N_L[1-P'_D-P'_L]$ is in the upper two levels $|1\rangle$ and $|2\rangle$. Radiative emission from levels $|1\rangle$ and $|2\rangle$ then follows, with the excited population dividing itself equally between $|D\rangle$ and $|L\rangle$. The resultant populations $N_D$ and $N_L$ in levels $|D\rangle$ and $|L\rangle$ is then:

$$N_D=0.5\ N_D[1+P_D-P_L]+0.5\ N_L[1+P'_D-P'_L]$$

$$N_L=0.5\ N_D[1+P_L-P_D]+0.5\ N_L[1+P'_L-P'_D] \quad (20)$$

The sequence of laser excitation followed by collisional relaxation and radiative emission is then iterated to convergence. In the second step, for example, the populations in Eq. (20) are taken as the initial populations for two independent computations, one assuming a population of $N_D$ in $|D\rangle$, with $|L\rangle$ unpopulated, and the second assuming a population of $N_L$ in $|L\rangle$, with $|D\rangle$ unpopulated.

Clearly, convergence is attained when the populations, post-radiative emission are the same as those prior to laser excitation. That us, analytically, we require [using Eq. (20)]

$$N_D=N_D$$

$$N_L=N_L. \quad (21)$$

Both of these conditions reduce to, $$N_D(1-P_D+P_L)=N_L(1+P'_D-P'_L) \quad (22)$$

If the total population is chosen to be normalized to $N_D+N_L=1$, then the final probabilities $\mathcal{P}_D$, $\mathcal{P}_L$ of populating states $|D\rangle$ and $|L\rangle$ is $$\mathcal{P}_D = \frac{1+P'_D-P'_L}{1-P_D+P_L+1+P'_D-P'_L} \quad (23)$$

$$\mathcal{P}_L = \frac{1-P_D+P_L}{1-P_D+P_L+1+P'_D-P'_L}$$

Results for the converged probabilities for the coupled double lambda system, for several sets of parameters, are shown in FIG. 3. Although the behavior as a function of laser parameters is somewhat different than that shown in FIG. 2, the results clearly show substantially enhanced enantiomeric ratios at various choices of control parameters. For example, at $\beta=1.5\times10^{-3}$, tuning $\Delta_1$ to 50 cm$^{-1}$ gives a preponderance of L whereas tuning to the $\Delta_1=-125$ cm$^{-1}$ gives more D.

Numerous parameters in the couple double-lambda system can be varied in order to alter the enantiomeric ratio. This includes the laser pulse shape, relative timing (e.g. positive or negative delay between pulses), pulse frequency and pulse power of each of the two lasers, etc. Examples are shown in FIGS. 4 through 7. In particular, FIGS. 4 and 5 show the effect of varying the ratio $\beta_0/\beta_1$ (with $\beta_1=10^{-4}$) for several values of $\Delta t=t_0-t_1$ whereas FIGS. 6 and 7 show the effect of varying $\Delta t$ for various laser field amplitudes. Once again it is clear that the probability of forming D or L is within the control of the operator.

Alterative Laser Distillation scenarios, based on the general principle outlined above, can be designed by the experienced practitioner.

We claim:

1. A process of enhancing the enantiomeric excess of a mixture of two mirror image enantiomers, denoted L and D, by irradiating the mixture with two or more achiral laser fields with some degree of coherence so as to selectively excite the mixture to a vibrational-rotational superposition state of an excited electronic state, which are themselves coupled by a radiation field, where the superposition state is comprised of states which differ in their symmetry with respect to reflection through a plane which interchanges the L and D enantiomers, and then allowing the mixture to radiate spontaneously to the ground electronic state.

2. The process of claim 1 where the laser fields are produced by pulsed lasers, and further comprising varying at least one of: laser pulse shapes, relative durations of laser pulses, peak timing of laser pulses, laser intensities, and thermodynamic properties of the mixture, to enhance the enantiomeric excess of a desired enantiomer.

3. The process of claim 1 where the enantiomers L and D are in thermal equilibrium.

4. The process of claim 1 where the process is used to differentiate between the directions right and left in space.

5. A process of enhancing the enantiomeric excess of a mixture containing two mirror image enantiomers, denoted L and D, comprising adding a molecule B to the L, D mixture so as to form weakly bound enantiomers L–B and B–D, then irradiating the L, D, B mixture with two or more achiral laser fields with some degree of coherence so as to selectively excite the L, D, B mixture to a vibrational-rotational superposition state of an excited electronic state, which are themselves coupled by a radiation field, where the superposition is comprised of states which differ in their symmetry with respect to reflection through a plane which interchanges LB and DB, subsequently allowing the L, D, B mixture to radiate spontaneously to the ground electronic state, and then removing the molecule B by standard chemistry.

6. The process of claim 5 where the laser fields are produced by pulsed lasers and further comprising varying at least one of: laser pulse shapes, relative durations of laser pulses, peak timing of laser pulses, laser intensities, and thermodynamic properties of the L, D, B mixture, to enhance the enantiomeric excess of a desired enantiomer.

7. The process of claim 5 where the enantiomers L and D are in thermal equilibrium.

8. The process of claim 5 where L and D are chiral alcohols and B is the ketone derived from the alcohol.

9. The process of claim 5 where the process is used to differentiate between the direction right and left in space.

10. A process of enhancing the enantiomeric excess of a mixture of two mirror image enantiomers, denoted L and D, by irradiating the mixture with two or more achiral laser fields with some degree of coherence so as to selectively excite the mixture to a vibrational-rotational superposition state of an excited electronic state, which are themselves coupled by a radiation field, where the superposition state is comprised of states which differ in their symmetry with respect to reflection through a plane which interchanges the L and D enantiomers, and then allowing the mixture to radiate spontaneously to the ground electronic state, an enantiomeric selectivity resulting from quantum interference induced by the laser irradiation.

* * * * *